US009376455B2

(12) United States Patent
Lee et al.

(10) Patent No.: US 9,376,455 B2
(45) Date of Patent: Jun. 28, 2016

(54) MOLECULAR LAYER DEPOSITION USING REDUCTION PROCESS

(71) Applicant: Veeco ALD Inc., Fremont, CA (US)

(72) Inventors: Sang In Lee, Los Altos Hills, CA (US); Chang Wan Hwang, Hwaseong-si (KR)

(73) Assignee: Veeco ALD Inc., Fremont, CA (US)

( * ) Notice: Subject to any disclaimer, the term of this patent is extended or adjusted under 35 U.S.C. 154(b) by 37 days.

(21) Appl. No.: 14/546,948

(22) Filed: Nov. 18, 2014

(65) Prior Publication Data

US 2015/0148557 A1    May 28, 2015

Related U.S. Application Data

(60) Provisional application No. 61/909,819, filed on Nov. 27, 2013.

(51) Int. Cl.
*C07F 7/00* (2006.01)
*B05D 1/00* (2006.01)
(Continued)

(52) U.S. Cl.
CPC .............. *C07F 5/068* (2013.01); *C07F 7/1836* (2013.01); *C23C 16/401* (2013.01); *C23C 16/403* (2013.01); *C23C 16/452* (2013.01); *C23C 16/45529* (2013.01); *C23C 16/45531* (2013.01); *C23C 16/45536* (2013.01); *C23C 16/45551* (2013.01); *C23C 16/45578* (2013.01)

(58) Field of Classification Search
CPC ..... C07F 5/068; C07F 7/1836; C23C 16/452; C23C 16/40; C23C 16/403; C23C 16/45536; C23C 16/45551; C23C 16/45578; C23C 16/45529; C23C 16/45531

USPC ........ 556/52, 173, 182; 427/255.28, 255.394, 427/562; 118/715
See application file for complete search history.

(56) References Cited

U.S. PATENT DOCUMENTS

2004/0224527 A1    11/2004    Sarigiannis et al.
2005/0064236 A1    3/2005    Lim et al.
(Continued)

FOREIGN PATENT DOCUMENTS

WO    WO 2010/138102 A1    12/2010

OTHER PUBLICATIONS

By George et al., Journal of Nanoscience and Nanotechnology, vol. 11, pp. 7948-7955 (2011).*
(Continued)

*Primary Examiner* — Porfirio Nazario Gonzalez
(74) *Attorney, Agent, or Firm* — Fenwick & West LLP

(57) ABSTRACT

A material is deposited onto a substrate by exposing the substrate to a metal-containing precursor to adsorb metal atoms of the metal-containing precursor to the substrate. The substrate injected with the metal-containing precursor is exposed to an organic precursor to deposit a layer of material by a reaction of the organic precursor with the metal atoms adsorbed to the substrate. The substrate is exposed to radicals of a reducing agent to increase reactivity of the material deposited on the substrate. The radicals of the reducing agent are produced by applying a voltage differential with electrodes to a gas such as hydrogen. The substrate may be exposed to radicals before and/or after exposing the substrate to the organic precursor. The substrate may be sequentially exposed to two or more different organic precursors. The material deposited on the substrate may be a metalcone such as Alucone, Zincone, Zircone, Titanicone, or Nickelcone.

13 Claims, 12 Drawing Sheets

(51) Int. Cl.

| | | |
|---|---|---|
| *C07F 5/06* | (2006.01) | |
| *C07F 7/18* | (2006.01) | |
| *C23C 16/40* | (2006.01) | |
| *C23C 16/452* | (2006.01) | |
| *C23C 16/455* | (2006.01) | |

(56) References Cited

U.S. PATENT DOCUMENTS

| | | |
|---|---|---|
| 2006/0213441 A1 | 9/2006 | Kobrin et al. |
| 2007/0145023 A1 | 6/2007 | Holber et al. |
| 2007/0243325 A1 | 10/2007 | Sneh |
| 2008/0075881 A1 | 3/2008 | Won et al. |
| 2008/0241387 A1 | 10/2008 | Keto |
| 2009/0197406 A1 | 8/2009 | Cao et al. |
| 2010/0037820 A1 | 2/2010 | Lee |
| 2010/0255625 A1 | 10/2010 | De Vries |
| 2011/0070380 A1 | 3/2011 | Shero et al. |

OTHER PUBLICATIONS

PCT International Search Report and Written Opinion, PCT Application No. PCT/US12/25095, Aug. 3, 2012, 18 pages.

PCT International Search Report and Written Opinion, PCT Application No. PCT/US12/25483, May 29, 2012, 10 pages.

\* cited by examiner

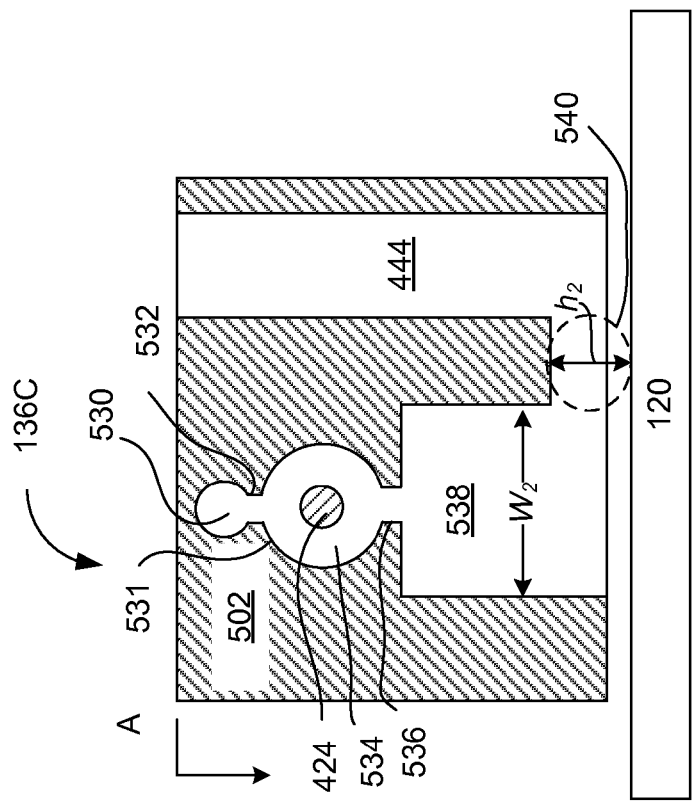
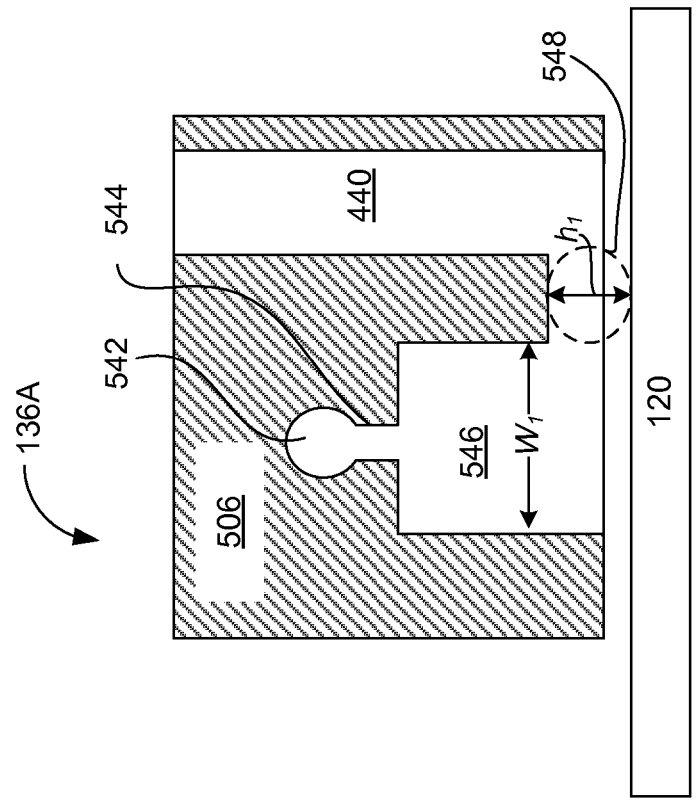
FIG. 5B
FIG. 5A

TMA + H* + ATPMOS + H* →

MOLECULAR LAYER DEPOSITION USING REDUCTION PROCESS

CROSS-REFERENCE TO RELATED APPLICATION

This application claims the benefit of U.S. Provisional Application No. 61/909,819, filed Nov. 27, 2013, which is hereby incorporated by reference in its entirety.

BACKGROUND

1. Field of Art

The disclosure relates to performing molecular layer deposition (MLD) on a substrate using radicals.

2. Description of the Related Art

MLD is a thin film deposition method for depositing molecules onto a substrate as a unit to form polymeric films on the substrate. In MLD, a molecular fragment is deposited during each reaction cycle. The precursors for MLD have typically been homobifunctional reactants. The MLD method is generally used for growing organic polymers such as polyamides on the substrate.

The precursors for MLD may be used to grow hybrid organic-inorganic polymers such as Alucone and Zircone. Alucone refers to an aluminum alkoxide polymer having carbon-containing backbones and may be obtained from a reaction of trimethylaluminum (TMA:$Al(CH_3)_3$) and ethylene glycol. Zircone refers to a hybrid organic-inorganic compound obtained from a reaction of a diol (e.g., ethylene glycol) with a zirconium precursor (e.g., zirconium t-butoxide $Zr[OC(CH_3)_3)]_4$, tetrakis(dimethylamido)zirconium $Zr[N(CH_3)_2]_4$).

SUMMARY

Embodiments relate to depositing material onto a substrate. The substrate is exposed to a metal-containing precursor to adsorb metal atoms of the metal-containing precursor to the substrate. The substrate exposed to the metal-containing precursor is exposed to an organic precursor to deposit a layer of material by a reaction of the organic precursor with the metal atoms adsorbed to the substrate. The substrate is exposed to radicals of a reducing agent to increase reactivity of the material deposited on the substrate. Exposing the substrate to metal-containing precursor, organic precursor, and radicals of the reducing agent may be repeated to deposit additional layers of the material onto the substrate.

In one embodiment, the substrate is exposed to radicals of the reducing agent to increase reactivity of the metal atoms with the organic precursor after injecting the metal-containing precursor onto the substrate and before injecting the organic precursor.

In one embodiment, the deposited material is a metalcone. The metal-containing precursor may comprise trimethylaluminum. The metal-containing precursor may comprise an aluminum-containing precursor, a titanium-containing precursor, a zinc-containing precursor, a zirconium-containing precursor, a nickel-containing precursor, or a combination thereof. The organic precursor may comprise at least one of a diol, a triol, an amino alcohol, an alkyl diamine, an alkyl phenol, an amino alkyl trialkoxy silane, an isocyanato alkyl trialkoxy silane, or a combination thereof.

In one embodiment, the reducing agent comprises at least one of hydrazine, ammonia, hydrogen gas, or a combination thereof. Exposing the substrate to radicals of the reducing agent may include injecting nitrogen gas to stabilize the reducing agent.

In one embodiment, exposing the substrate to the organic precursor may include sequentially exposing the substrate to multiple organic precursors. The substrate injected with the metal-containing precursor is exposed to a first organic precursor to deposit the layer of material by a reaction of the first organic precursor with the metal atoms adsorbed to the substrate. The substrate injected with the first organic precursor is exposed to radicals of the reducing agent to increase reactivity of the material deposited on the substrate with a second organic precursor after exposing the substrate to the first organic precursor. The substrate injected with the first organic precursor is exposed to the second organic precursor to retain or lengthen hydrocarbon bridges of the deposited layer of material. The first organic precursor may be 4-ethylphenol and the second organic precursor may be 3-aminopropyltrimethoxysilane, or the reverse. The first organic precursor may be 3-aminopropyltrimethoxysilane and the second organic precursor may be 3-isocyanatopropyltriethoxysilane, or the reverse.

Embodiments also relate to a product comprising material deposited on a substrate. The product is produced by the method described herein.

Embodiments relate to an apparatus for depositing a layer of material onto a substrate. The apparatus includes a first injector, a moving mechanism, a second injector, and a radical reactor. The first injector has a first reaction chamber opening towards a surface of a substrate to inject a metal-containing precursor onto the surface and to cause metal atoms of the metal-containing precursor to adsorb to the surface of the substrate. The moving mechanism is configured to cause a relative movement between the first substrate and the first injector. The second injector is disposed on a path of the relative movement and has a second reaction chamber opening towards the surface of the substrate to inject an organic precursor onto the surface of the substrate injected with the metal-containing precursor and to deposit a layer of material onto the substrate by a reaction of the organic precursor with the metal atoms adsorbed to the substrate. The radical reactor is configured to generate an inject radicals of a reducing agent onto the substrate injected with the organic precursor.

In one embodiment, the first injector is formed with an exhaust portion a constriction zone connecting the exhaust portion and the first reaction chamber. A width of the first reaction chamber parallel to the path of relative movement exceeds a height between an upper surface of the constriction zone and the surface of the substrate.

In one embodiment, the apparatus includes a third injector on the path of the relative movement. The third injector is configured to inject an inert gas onto the substrate to remove metal-containing precursor that is physisorbed on the substrate.

BRIEF DESCRIPTION OF THE DRAWINGS

FIG. 5A is a cross-sectional diagram illustrating an injector of FIG. 4, according to one embodiment.

FIG. 5B is a cross-sectional diagram illustrating a radical reactor of FIG. 4, according to one embodiment.

DETAILED DESCRIPTION OF EMBODIMENTS

Figure 1:
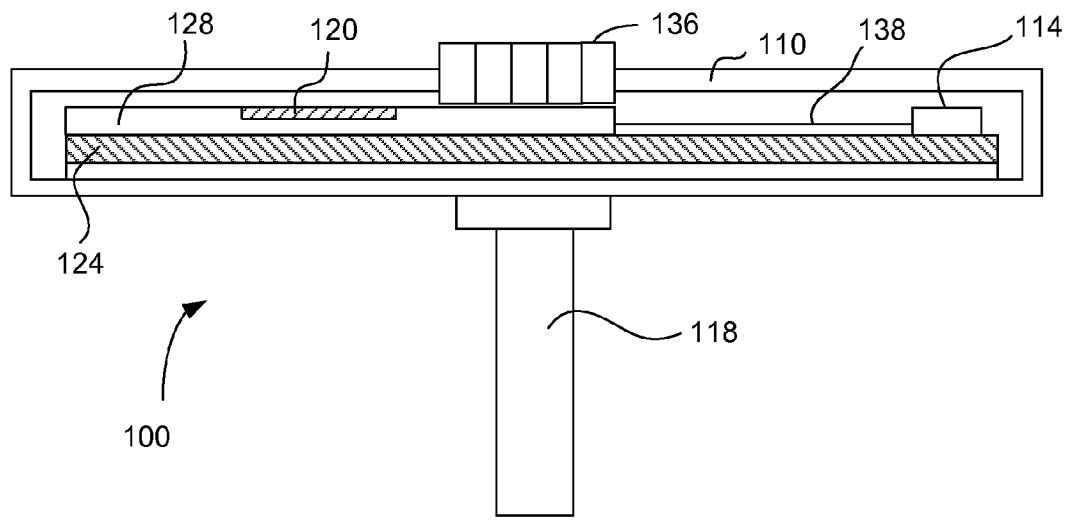
FIG. 1 is a cross-sectional diagram of a linear deposition device for performing molecular layer deposition, according to one embodiment.

Embodiments are described herein with reference to the accompanying drawings. Principles disclosed herein may, however, be embodied in many different forms and should not be construed as being limited to the embodiments set forth herein. In the description, details of well-known features and techniques may be omitted to avoid unnecessarily obscuring the features of the embodiments.

In the drawings, like reference numerals in the drawings denote like elements. The shape, size and regions, and the like, of the drawing may be exaggerated for clarity.

Embodiments relate to performing a molecular layer deposition (MLD) process using radicals of a reducing agent (e.g., hydrogen radicals H*) to increase the deposition rate and/or improve polymeric characteristics of material deposited on a substrate. After injecting a metal-containing precursor (e.g., trimethylaluminum (TMA)) and an organic precursor (e.g., 4-ethylphenol) onto the substrate, radicals of the reducing agent are injected to deposit a next layer of metalcone. By using radicals of a reducing agent instead of radicals of an oxidizing gas, carbon bridges in the deposited material are retained, thereby increasing the deposition rate and resulting in metalcones exhibiting higher polymeric characteristics.

Linear Deposition Device

Figure 2:
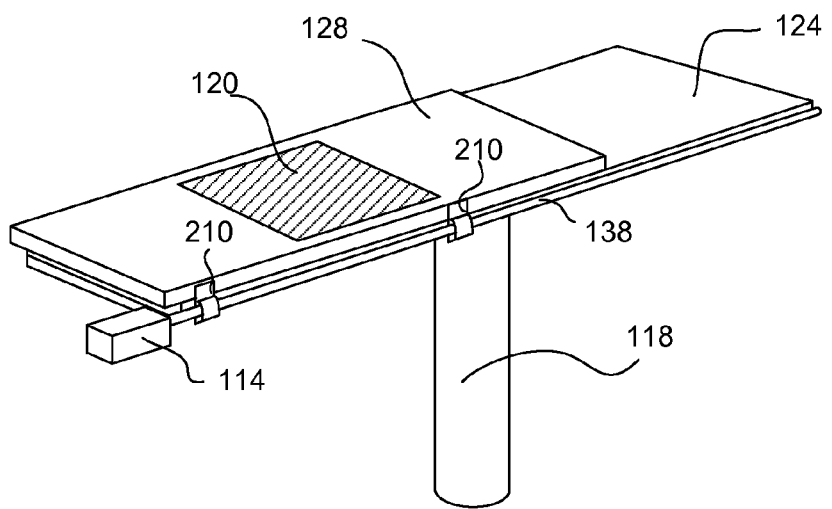
FIG. 2 is a perspective view of a linear deposition device, according to one embodiment.

FIG. 1 is a cross-sectional diagram of a linear deposition device 100 for performing an MLD process, according to one embodiment. FIG. 2 is a perspective view of the linear deposition device 100 (without chamber walls to facilitate explanation), according to one embodiment. The linear deposition device 100 may include, among other components, a support pillar 118, a process chamber 110, and one or more reactors 136. The reactors 136 may include one or more of injectors and one or more radical reactors. Each of the injectors injects purge gas, metal-containing precursor, or organic precursor onto the substrate 120.

The process chamber 110 enclosed by the walls may be maintained in a vacuum state to prevent contaminants from affecting the deposition process. The process chamber 110 contains a susceptor 128 which receives a substrate 120. The susceptor 128 is placed on a support plate 124 for a sliding movement. The support plate 124 may include a temperature controller (e.g., a heater or a cooler) to control the temperature of the substrate 120. The linear deposition device 100 may also include lift pins (not shown) that facilitate loading of the substrate 120 onto the susceptor 128 or dismounting of the substrate 120 from the susceptor 128.

In one embodiment, the linear deposition device 100 includes a moving mechanism configured to cause a relative movement between the substrate 120 and the reactors 136. The moving mechanism includes the motor 114 and the extended bar 138. The susceptor 128 is secured to one or more brackets 210 that move across the extended bar 138 with screws formed thereon. The brackets 210 have corresponding screw threads formed in their holes receiving the extended bar 138. The extended bar 138 is secured to a spindle of a motor 114, and hence, the extended bar 138 rotates as the spindle of the motor 114 rotates. The rotation of the extended bar 138 causes the brackets 210 (and therefore the susceptor 128) to make a linear movement on the support plate 124. In other words, the brackets 210 convert the rotational motion of the extended bar 138 into linear motion parallel to the extended bar 138. By controlling the speed and rotation direction of the motor 114, the speed and the direction of the linear movement of the susceptor 128 can be controlled along a path of relative movement. The use of a motor 114 and the extended bar 138 is merely an example of the moving mechanism causing relative movement between the susceptor 128 and the reactors 136. Alternatively or additionally, the moving mechanism moves the susceptor 128 by various other means (e.g., gears, rack, and/or pinion at the bottom, top, or side of the susceptor 128). Instead of (or in addition to) moving the susceptor 128 relative to the reactors 136, the moving mechanism may move the reactors 136 relative to the susceptor 128.

Rotating Deposition Device

Figure 3:
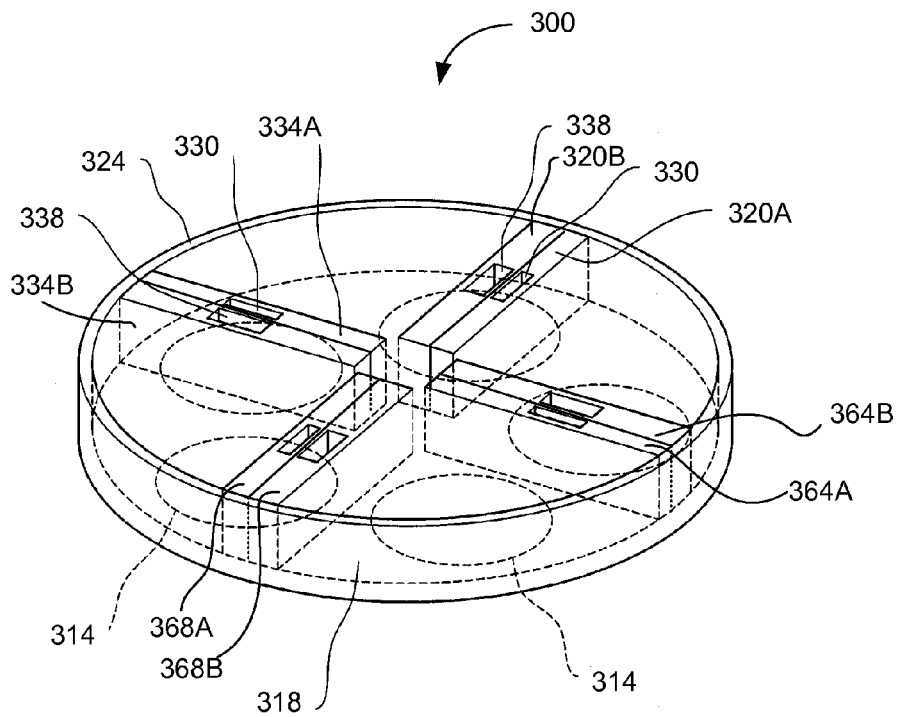
FIG. 3 is a perspective view of a rotating deposition device for performing molecular layer deposition, according to one embodiment.

FIG. 3 is a perspective view of a rotating deposition device 300, according to one embodiment. Instead of (or in addition to) using the linear deposition device 100 of FIG. 1, the rotating deposition device 300 may perform the deposition process. The rotating deposition device 300 may include, among other components, reactors 320A, 320B, 334A, 334B, 364A, 364B, 368A, 368B (collectively referred to as reactors 320, 334, 364, and 368), a susceptor 318, and a container 324 enclosing these components. A set of reactors (e.g., 320A and 320B) of the rotating deposition device 300 correspond to the reactors 136 of the linear deposition device 100, as described above with reference to FIG. 1. The susceptor 318 secures the substrates 314 in place. The reactors 320, 334, 364, and 368 are placed above the substrates 314 and the susceptor 318. The rotating deposition device 300 may include a moving mechanism to cause relative rotation between the susceptor 318 and the reactors 320, 334, 364, and 368. The relative rotation subjects the substrates 314 to different processes corresponding to the different reactors 320, 334, 364, and 368 as the substrates 314 follow a circular path of relative movement. The rotating deposition device 300 may include a motor and connective components (not shown) to transfer rotational motion from the motor to the susceptor 318.

One or more of the reactors 320, 334, 364, or 368 are connected to gas pipes (not shown) to provide source precursor, reactor precursor, purge gas, and/or other materials. The materials provided by the gas pipes may be (i) injected onto the substrate 314 directly by the reactors 320, 334, 364, or 368, (ii) after mixing in a chamber inside the reactors 320, 334, 364, or 368, or (iii) after conversion into radicals by plasma generated within the reactors 320, 334, 364, or 368. After the materials are injected onto the substrate 314, the redundant materials may be exhausted through outlets 330 or 338. The interior of the rotating deposition device 300 may also be maintained in a vacuum state.

Although the following example embodiments are described primarily with reference to the reactors 136 in the linear deposition device 100, the same principles and operations can be applied to the rotating deposition device 300 or other types of deposition device.

Example Reactors

Figure 4:
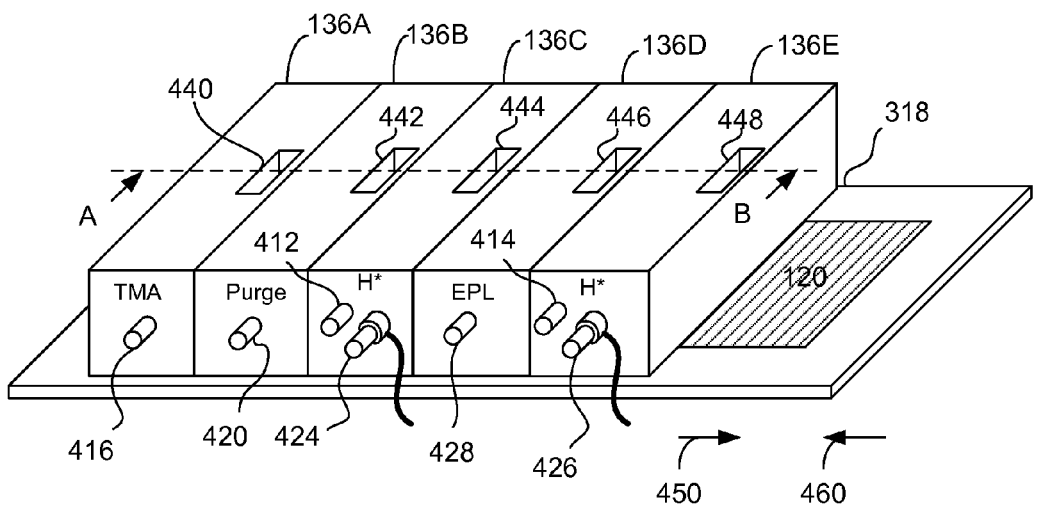
FIG. 4 is a perspective view of reactors in a deposition device of FIG. 1, according to one embodiment.

FIG. 4 is a perspective view of reactors 136A through 136E (collectively referred to as the "reactors 136") in the deposition device 100 of FIG. 1, according to one embodiment. In FIG. 4, the reactors 136A through 136E are placed in tandem adjacent to each other. In other embodiments, the reactors 136A through 136E may be placed at a distance from each other. As the substrate 120 moves from the left to the right (as shown by arrow 450), the substrate 120 is sequentially injected with materials by the reactors 136A through 136E to deposit a layer of material onto the substrate 120. Instead of (or in addition to) the substrate 120 being moved relative to the reactors 136, the reactors 136 may be moved relative to the substrate 120 (e.g., from right to left while injecting materials).

In one embodiment, after moving the substrate 120 from the left to the right, the substrate 120 may be moved from right to left (as shown by arrow 460) to expose the substrate 120 and the deposited material thereon to a different sequence of materials compared to moving the substrate 120 from left to right. In another embodiment, the substrate 120 is repeatedly exposed to the same sequence of materials. The exposure of the substrate 120 to the same sequence of materials may be accomplished by using the rotating deposition device 300 or shutting off the gas and radicals while the substrate 120 is moving in the direction shown by arrow 460 and turning back on the gas and radicals while the substrate 120 is moving in the direction shown by arrow 450.

The reactors 136A, 136B, and 136D (also referred to as injectors) inject gas or a mixture of gas onto the substrate 120 received via pipes 416, 420, and 428, respectively. Excess gas remaining after injection onto the substrate 120 is exhausted via exhaust portions 440, 442, and 446. The structure of the injectors 136A, 136B, and 136D is described below in detail with reference to FIG. 5A.

The reactors 136C and 136E (also referred to as radical reactors) generate radicals of gas and inject the radicals onto the substrate 120. The radical reactor 136C is connected to a pipe 412 to receive gas from a source. An electrode 424 extends across the length of the radical reactor 136C. By applying voltage across the electrode 424 and the body of the radical reactor 136C, the injected gas is converted into radicals. The radicals are injected onto the substrate 120, gas that has reverted to an inactive state and any remaining radicals are discharged from the radical reactor 136C via an exhaust portion 444. The reactor 136E has the same structure as the reactor 136C and includes a pipe 414, an electrode 426, and an exhaust portion 448. The structure of the radical reactors 136C and 136E is described in detail below with reference to FIG. 5B.

Example Injector

FIG. 5A is a cross-sectional diagram illustrating the injector 136A of FIG. 4, according to one embodiment. The injector 136A includes a body 506 formed with a gas channel 542, perforations (e.g., slits or holes) 544, a reaction chamber 546, a constriction zone 548, and an exhaust portion 440. Gas supplied from the pipe 416 to the gas channel 542 is injected into the reaction chamber 546 via the perforations 544. The reaction chamber 546 opens toward the surface of the substrate 120, so gas filling the reaction chamber 546 is injected onto the substrate 120. The injected gas flows through the reaction chamber 546, the constriction zone 548, and the exhaust portion 440.

The constriction zone 548 has a height $h_1$ that is smaller than the width $W_1$ of the reaction chamber 546. The width $W_1$ is measured parallel to the path of relative movement between the substrate 120 and the reactors 136. The height $h_1$ is measured between an upper surface of the constriction zone 548 and the surface of the substrate 120. The reaction chamber's cross-sectional area $A_1$, which is perpendicular to the downward flow of gas from the gas channel 542 toward the substrate 120, exceeds the constriction zone's cross-sectional area $A_2$, which is perpendicular to the lateral flow of gas over the substrate 120 from the reaction chamber 546 to the exhaust portion 440. As the cross-sectional area decreases from the reaction chamber 546 to the constriction zone 548, the gas flowing from the reaction chamber 546 into the constriction zone 548 undergoes an increase in velocity and decrease in pressure in due to the Venturi effect. The increased velocity in the constriction zone 548 increases the rate of convective mass transfer between material deposited on the substrate 120 (and any gas physisorbed on the substrate 120). In addition, the decreased pressure in the constriction zone 548 reduces the equilibrium concentration of gas physisorbed on the substrate 120 (or of volatile material deposited on the substrate 120). The increased velocity and decreased pressure accordingly remove excess gas and/or material from the substrate 120 more efficiently.

The injectors 136B and 136D may have the same or similar structure as the injector 136A, and therefore, the detailed description thereof is omitted herein for the sake of brevity.

In one embodiment, the injectors 136A, 136B, and 136D inject, respectively, a metal-containing precursor (e.g., trimethylaluminum), a purge gas (e.g., an inert gas such as argon gas Ar or nitrogen gas $N_2$), and an organic precursor (e.g., 4-ethylphenol). As a result of injecting these materials in sequence, a metalcone (e.g., Alucone) is deposited on the substrate 120.

Example Radical Reactor

FIG. 5B is a cross-sectional diagram illustrating the radical reactor 136C of FIG. 4, according to one embodiment. The radical reactor 136C includes a body 502 formed with a gas channel 530, a plasma chamber 534, a passage 532 connecting the gas channel 530 and the plasma chamber 534, perforations (e.g., slits or holes) 536, a reaction chamber 538, a constriction zone 540, and an exhaust portion 444. The radical reactor 136C includes an inner electrode 424 and an outer electrode 531 surrounding the plasma chamber 534 (the outer electrode 531 may be integral to the metallic body 502). A gas or a mixture of gases supplied by the pipe 412 to channel 530 is injected into the plasma chamber 534 via the passage 532. By applying a voltage difference between the inner electrode 424 and the outer electrode 531, plasma is generated in the plasma chamber 534. For example, the voltage difference is generated by a DC (direct current) pulse generator at 150 W and 300 kHz.

As a result of generating the plasma, radicals of the gas or the mixture of gases are formed within the plasma chamber 534. Since the plasma chamber 534 is located away from the substrate 120 (i.e., the radical reactor 136C is a remote-type plasma generator), the substrate 120 or any devices formed on the substrate 120 are not damaged by the process of generating the radicals. The generated radicals are injected into the reaction chamber 538 via the perforations 536. The reaction chamber 538 opens toward the surface of the substrate 120, so a region of the substrate 120 below the reaction chamber 538 is exposed to the injected radicals. In one embodiment, the generated radicals heat the surface of the substrate to a temperature below 120° C., which beneficially prevents the substrate from melting. For example, the substrate is commercial low-density polyethylene, which has a melting point between 105° C. to 115° C.

In one embodiment, hydrogen gas $H_2$ is provided into the reactor 136C to generate hydrogen radicals H*. In order to stabilize the hydrogen radicals H*, nitrogen gas $N_2$ may also be injected into the radical reactor 136C in conjunction with the hydrogen gas $H_2$. The mixture ratio between hydrogen gas $H_2$ and the nitrogen gas $N_2$ is not critical and may take any ratio from 50:50 to 99:1. It is advantageous to use hydrogen radicals H*, among other reasons, to perform the MLD process without breaking the carbon chains in the organic precursor. Compared to using radicals of oxidizing gas (e.g., oxygen radicals O*), the deposition rate of the deposited material can be increased and the polymeric properties of the deposited material can be improved.

Excess radicals and/or gas reverted to an inactive state from the radicals pass through the constriction zone 540 and are discharged via the exhaust portion 444. In one embodiment, a width $W_2$ of the reaction chamber 538 is greater than a height $h_2$ of the constriction zone 540, thereby increasing the velocity and decreasing the pressure of excess radicals and/or gas flow through the Venturi effect as described previously. Accordingly, the rate of convective mass transfer is increased and the equilibrium concentration of physisorbed gas on the substrate 120 (or excess material on the substrate 120) is decreased, so excess gas and/or radicals are more efficiently removed (at least partially) from the substrate 120.

The radical reactor 136E has the same or similar structure as the radical reactor 136C, and therefore, the detailed description of the radical reactor 136E is omitted herein for the sake of brevity.

Deposition of Metalcone Layers

Figure 6:
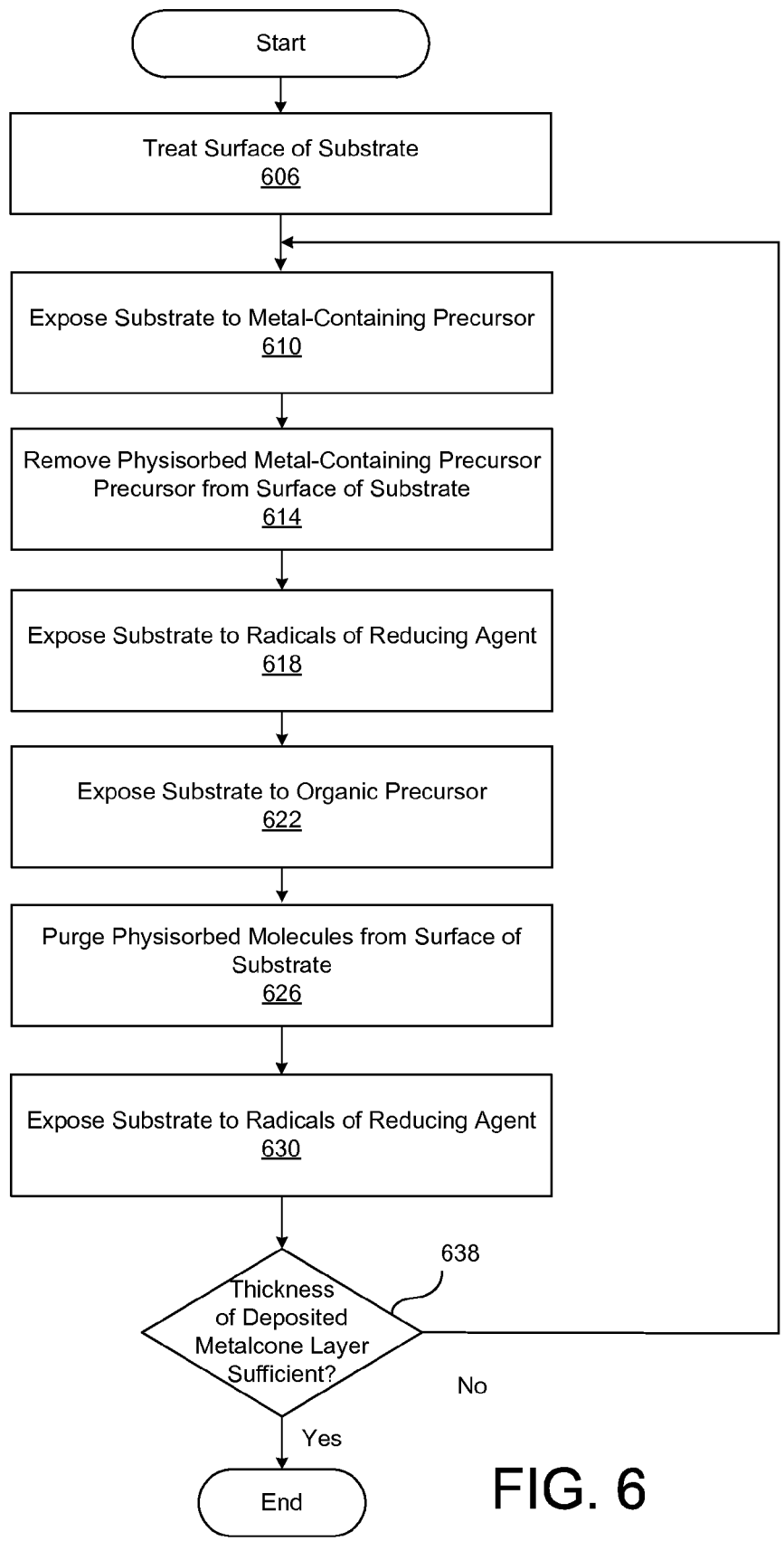
FIG. 6 is a flowchart illustrating a method of depositing material onto a substrate, according to one embodiment.

FIG. 6 is a flowchart illustrating deposition of metalcone layers using a MLD process, according to one embodiment. The following embodiments are described primarily with reference to using trimethylaluminum (TMA) as a metal-containing precursor and 4-ethylphenol (4-EPL) as an organic precursor to deposit Alucone, but different combinations of metal-containing precursors and organic precursors may be used to deposit the same or a different metalcone.

Figure 7A:
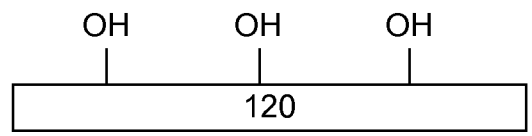
FIGS. 7A through 7G are conceptual diagrams illustrating materials deposited on the substrate when the substrate undergoes processing steps for performing MLD, according to one embodiment.

First, the surface of the substrate 120 is treated 606, for example, hydroxylated, to facilitate the subsequent processing steps. Referring to FIG. 7A, the surface of the substrate 120 is illustrated after hydroxylation. The substrate 120 is covered with hydroxyls OH to facilitate subsequent reaction with a metal-containing precursor.

Figure 7B:
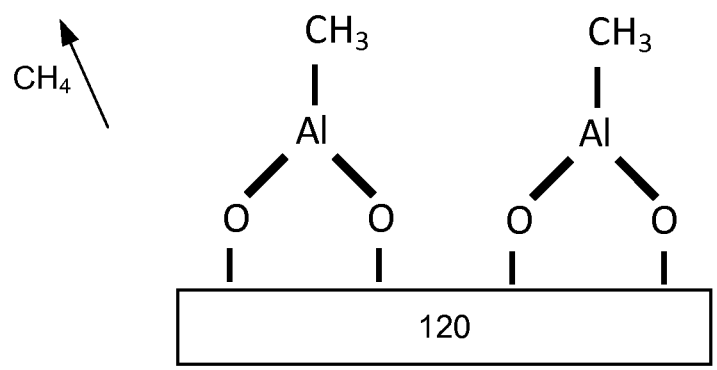

The substrate 120 below the injector 136A is exposed 610 to metal-containing precursor (e.g., TMA). Consequently, metal atoms (e.g., aluminum atoms) from the metal-containing precursor (e.g., TMA) are adsorbed to oxygen atoms from the hydroxyl groups attached to the surface of the substrate 120, as shown in FIG. 7B. When the metal-containing precursor is TMA, methane gas $CH_4$ is formed as a byproduct and is discharged through the exhaust portion 440 along with excess TMA. If the substrate 120 is exposed 610 to another metal-containing precursor, a different byproduct than methane $CH_4$ may be formed.

Metal-containing precursors include an aluminum-containing precursor (e.g., TMA, dimethyethylamine alane $AlH_3N(CH_3)_2(C_2H_5)$ (DMEAA), dimethylaluminum hydride $Al(CH_3)_2H$ (DMAH), dimethylaluminum isopropoxide $(CH_3)_2AlOCH(CH_3)_2$ (DMAI)), which is injected to deposit Alucone.

Metal-containing precursors include a titanium-containing precursor (e.g., titanium tetrachloride $TiCl_4$, tetrakis(dimethylamino)titanium $[N(CH_3)_2]_4Ti$ (TDMAT), tetrakis(ethylmethylamino)titanium $[C_2H_5NCH_3]_4Ti$ (TEMATi), another tetrakis(dialkylamino)titanium), which is injected to deposit Titanicone.

Metal-containing precursors include a zirconium-containing precursor (e.g., tetrakis(dimethylamino)zirconium $[(CH_3)_2N]_4Zr$ (TDMAZ), tetrakis(ethylmethylamino)zirconium $[(C_2H_5)(CH_3)N]_4Zr$ (TEMAZr), another tetrakis(dialkylamino)zirconium), which is injected to deposit Zircone.

Metal-containing precursors include a zinc-containing precursor (e.g., diethylzinc $(C_2H_5)_2Zn$, another dialkylzinc), which is injected to deposit Zincone.

Metal-containing precursors include a nickel-containing precursor such as bis(1,4-di-isopropyl-1,3-diazabutadienyl) nickel $Ni(^iPr\text{-}DAD)_2$ or a nickel dialkylamino alkoxide complex (e.g., nickel bis(1-dimethylamino-2-methyl-2-propanolate) $Ni[OC(CH_3)_2CH_2N(CH_3)_2]_2$, nickel bis(1-dimethylamino-2-methyl-2-butanolate) $Ni[OC(CH_3)(C_2H_5)CH_2N(CH_3)_2]_2$), which is injected to deposit Nickelcone.

The substrate 120 below the injector 136B is purged to partially or entirely remove 614 physisorbed metal-containing precursor molecules from the surface of the substrate 120 by controlling the flow rate of purge gas (e.g., Ar). Purging may be obviated if the removal process performed by the constriction zone 548 of the injector 136A is sufficient. In such a case, the reactor 136B may be omitted.

Figure 7C:
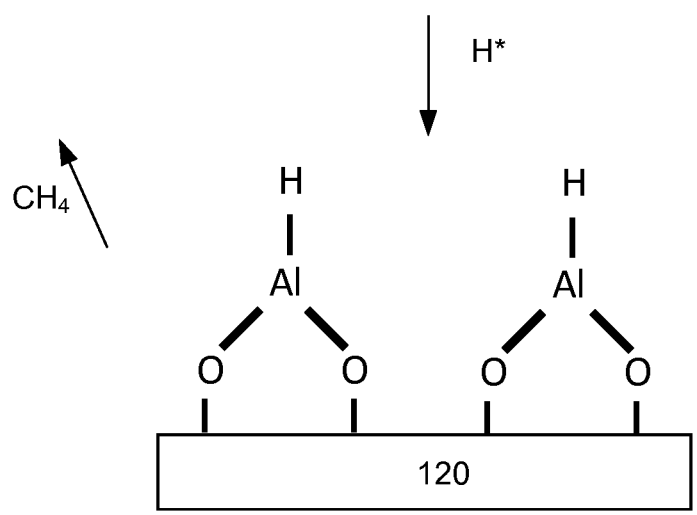

The substrate 120 below the radical reactor 136C is exposed 618 to hydrogen radicals H* (in conjunction with nitrogen radicals N* if nitrogen gas $N_2$ was mixed with hydrogen gas $H_2$ in the radical reactor 136C). As a result, metal hydrides (e.g., aluminum hydrides or intermediates thereof) are formed on the surface of the substrate 120, as shown in FIG. 7C. Methane gas $CH_4$ may be formed as a byproduct and is discharged through the exhaust portion 444 along with excess radicals and/or gas. If the substrate 120 is exposed 610 to another metal-containing precursor, a different byproduct than methane gas $CH_4$ may be formed. In embodiments where the metal-containing precursor reacts with an organic precursor having oxidative ligands (e.g., —OH, —COOH, —NH$_2$, —OCH$_3$), exposing 618 the substrate 120 to hydrogen radicals H* may be omitted. In such a case, the radical reactor 136C may be omitted.

Figure 7D:
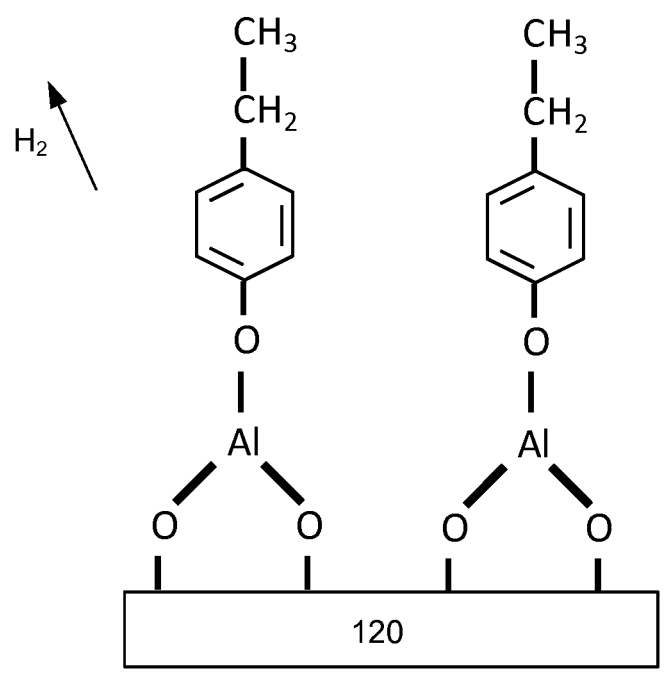

The substrate 120 below the injector 136D is then exposed 622 to the organic precursor (e.g., 4-ethylphenol) to deposit a layer of material. Since the metal hydrides are reactive, the metal hydrides react with the organic precursor, forming a layer of metalcone on the surface of the substrate 120. An example structure of a metalcone formed on the substrate 120 by injecting 4-ethylphenol is illustrated in FIG. 7D. Hydrogen gas $H_2$ is also formed as a byproduct and is discharged via the exhaust portion 446.

Organic precursors include homobifunctional organic reactants such as diols (e.g., 2,3-butanediol $H_3C(CHOH)_2CH_3$, 1,4-butanediol $HOCH_2(CH_2)_2CH_2OH$, 1,5-pentanediol $HOCH_2(CH_2)_3CH_2OH$) and triols (e.g., glycerol).

Organic precursors include heterobifunctional organic reactants such as amino alcohols (e.g., 2-aminoethanol $H_2NCH_2CH_2OH$, 4-aminophenol $H_2N(C_6H_4)OH$); alkyldiamines (e.g., ethylene diamine $H_2N(CH_2)_2NH_2$); amino alkyl trialkoxy silanes (e.g., 3-amino-propyl trimethoxysilane $H_2N(CH_2)_3Si(OCH_3)_3$ (APTMOS)); and isocyanatoalkyl trialkoxy silanes (e.g., 3-isocynatopropyl triethoxy silane $OCN(CH_2)_3Si(OC_2H_5)_3$ (ICPTEOS)).

A purging process may then be performed to purge 626 physisorbed molecules from the surface of the substrate 120 by an injector (not shown). This purging process may be omitted.

Figure 7E:
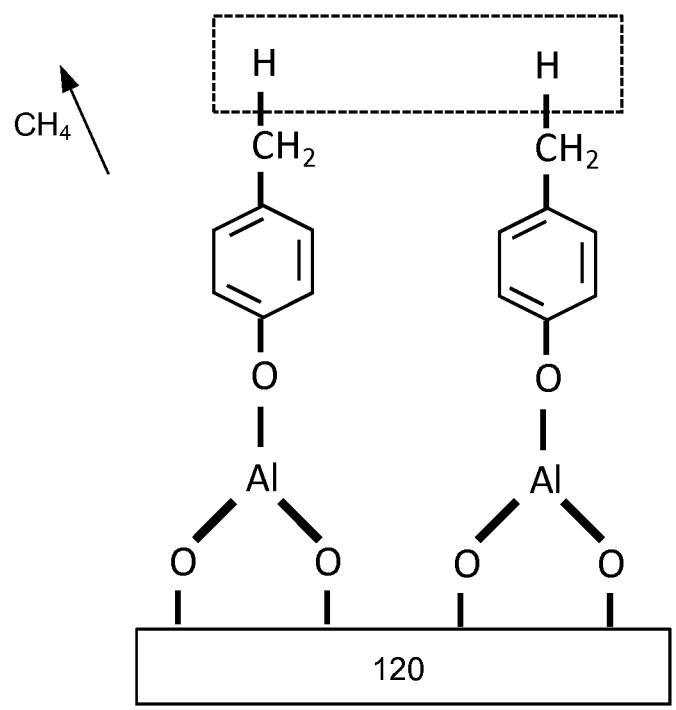

Subsequently, the substrate 120 below the radical reactor 136E is exposed 630 to hydrogen plasma $H_2$ or hydrogen radicals H* to replace terminal functional groups of the deposited with hydrogen atoms H. As a result, the reactivity of material deposited on the substrate 120 is increased with respect to the metal-containing precursor. Methane gas $CH_4$ is formed as a byproduct and is discharged by the radical reactor 136E. If the substrate 120 is exposed 622 to a different organic precursor, other byproducts may be formed. The hydrogen radicals H* selectively react with methyl groups rather than breaking the bonds between carbon atoms in aromatic rings of the metalcone. For example, the bonds between carbons forming the aromatic ring in 4-ethylphenol are unbroken, and therefore, the aromatic benzene ring illustrated in FIG. 7E remains intact. FIG. 7E illustrates the structure of material deposited on the substrate 120 terminating with hydrogen atoms, which are the smallest ligands. Other, larger ligands may hinder the adsorption of subsequently injected precursor and thereby reduce the deposition rate.

Figure 7F:
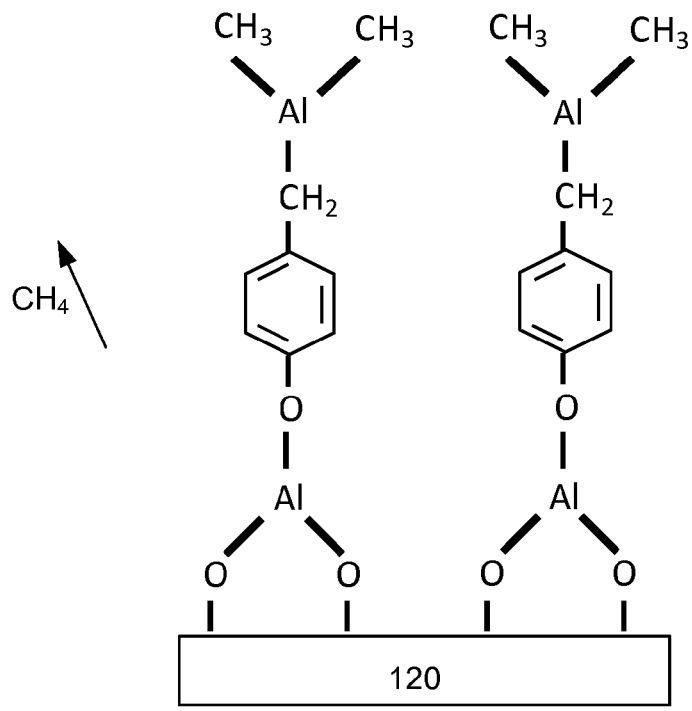

The thickness of the deposited metalcone layer is determined. If 638 the thickness of the metalcone layer is sufficient (i.e., exceeds a threshold thickness), the process terminates. If 638 the thickness of the metalcone is insufficient (i.e., does not exceed a threshold thickness), the process returns to exposing 610 the substrate 120 to the metal-containing precursor. FIG. 7F is a diagram illustrating the result of injecting TMA as the metal-containing precursor, for example, using the injector 136A onto a hydrogen atom of the terminal methyl groups, as illustrated in FIG. 7E. When the metal-containing precursor is TMA, methane gas $CH_4$ is formed as a byproduct and is discharged through the exhaust portion 440 along with excess TMA. If the substrate 120 is exposed 610 to another metal-containing precursor, a different byproduct may be produced.

Figure 7G:
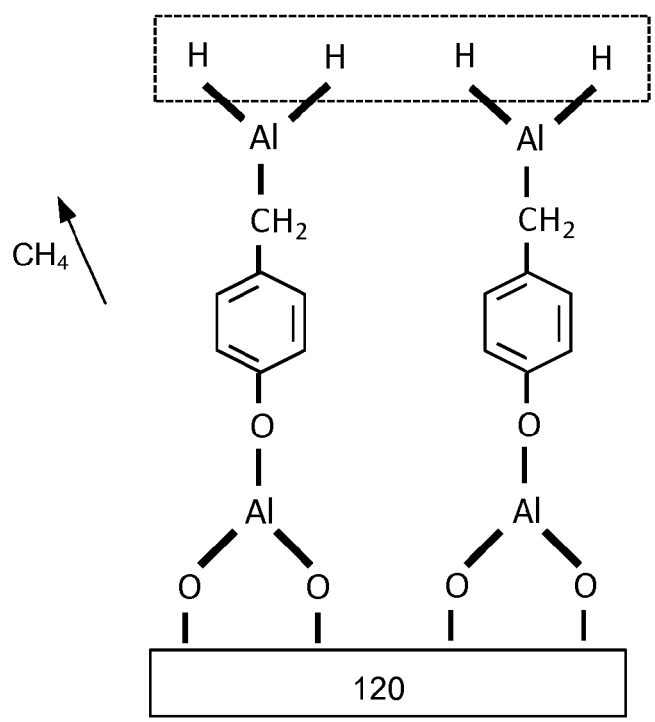

The process may then proceed to remove 614 the physisorbed metal-containing precursor (if necessary) and then to expose 618 the substrate 120 to the radicals of a reducing agent (e.g., hydrogen radicals H*). FIG. 7G illustrates the result of exposing the structure of FIG. 7F to hydrogen radicals H*. The exposure to hydrogen radicals H* also generates a methane gas $CH_4$ byproduct, but if the substrate 120 is exposed 610 to another metal-containing precursor, another byproduct gas may be formed. The subsequent processes of exposing 622 the substrate 120 to the organic precursor, purging 626 the physisorbed molecules, and exposing 630 the substrate 120 to the radicals of reducing agent may be performed on the substrate 120.

Figure 8A:
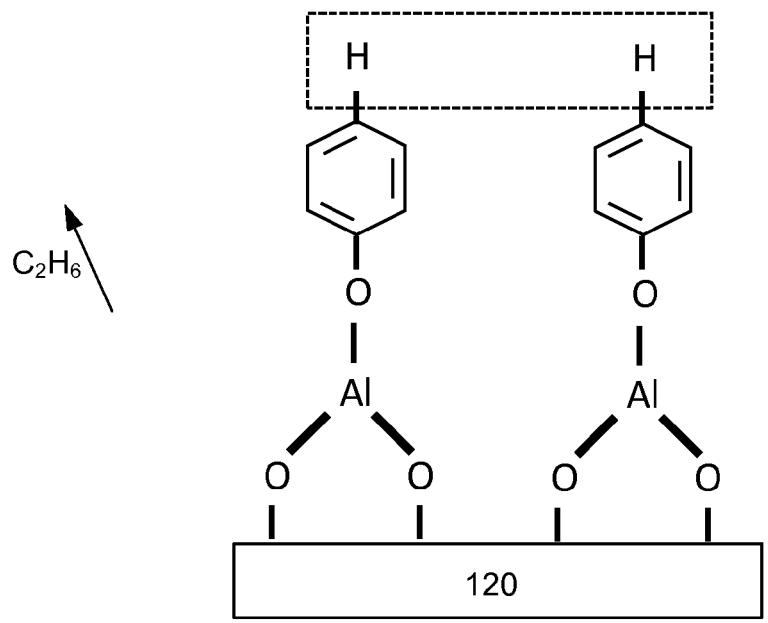
FIGS. 8A through 8C are conceptual diagrams illustrating deposition of a material with an alternative structure using the MLD process, according to one embodiment.

It is also surmised that if the structure of FIG. 7D is exposed 630 to a larger amount of hydrogen radicals H* or higher plasma power, the structure of FIG. 8A may be obtained instead of the structure of FIG. 7E. In practice, the substrate 120 may be formed with a mixture of materials having the structure of FIG. 7E and the structure of FIG. 8A.

Figure 8B:
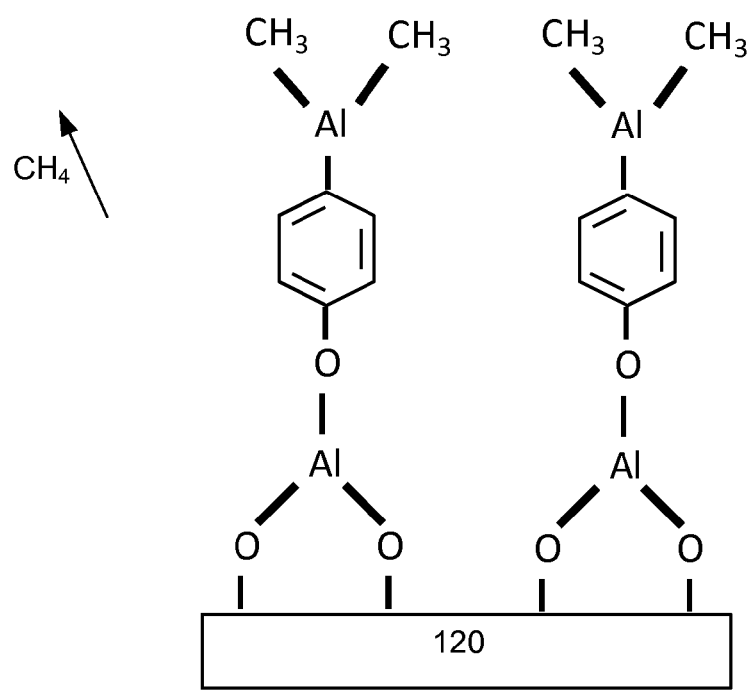
Figure 8C:
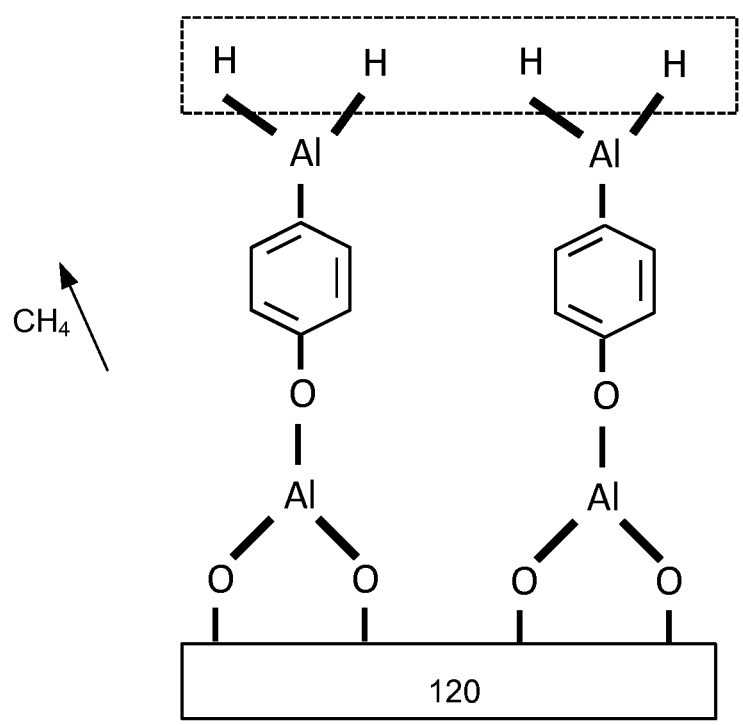

Compared to the structure of FIG. 7D, the structure of FIG. 8A lacks a methyl group —$CH_3$ attached to the aromatic benzene ring. Further, when the structure of FIG. 8A is obtained, ethane gas $C_2H_6$ may be generated as a byproduct. If the substrate 120 is exposed 622 to a different organic precursor, then a different byproduct may be obtained from alkyl groups substituted to the benzene ring. When the structure of FIG. 8A is exposed 610 to TMA, the structure of FIG. 8B is obtained. The subsequent process of exposing 618 or 630 the substrate 120 to hydrogen radicals H* results in the structure of FIG. 8C while producing methane gas $CH_4$ as a byproduct. If a different metal-containing precursor is injected, then a different byproduct gas may be produced.

One of many advantages of using reducing radicals (e.g., radical hydrogen H*) instead of oxidizing radicals is that the carbon bridges in the formed metalcones are maintained. Since the carbon bridges are retained, the deposition rate of metalcone is increased. Moreover, the formed metalcone retains polymeric characteristics since the carbon bridges remain intact.

Instead of using hydrogen radicals H*, radicals of other reducing agents such as hydrazine $N_2H_4$ or ammonia $NH_3$ may also be used. Plasmas generated from these reducing agents contain hydrogen radicals H* and provide similar results to using hydrogen radicals H* generated from hydrogen gas $H_2$.

Figure 9:
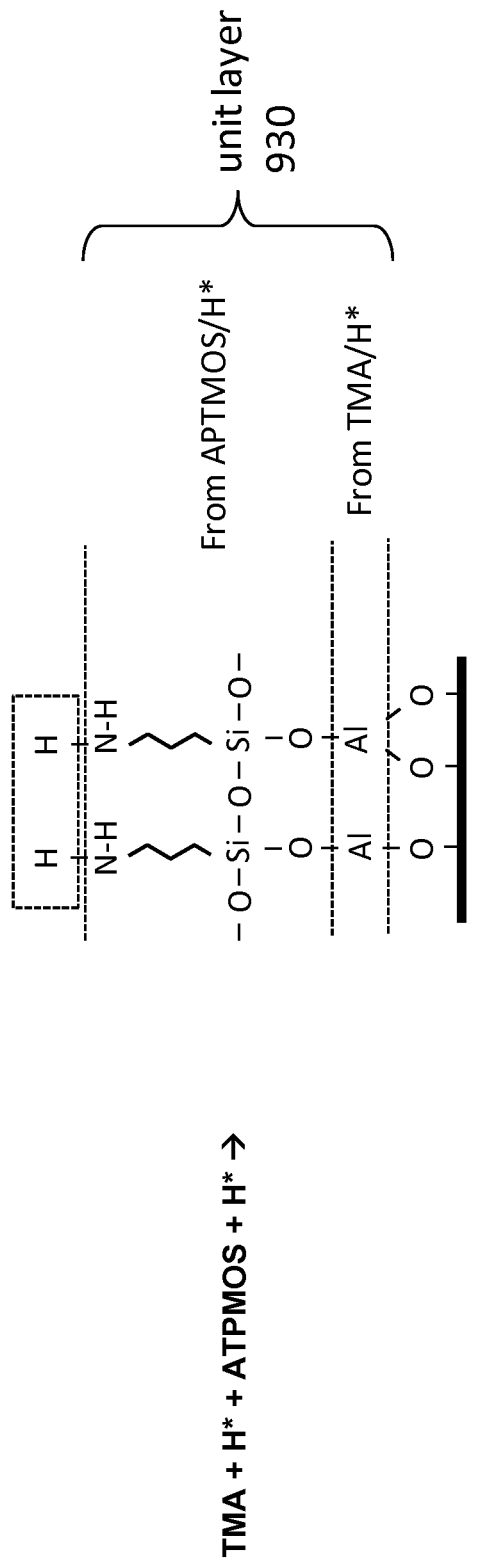
FIG. 9 is a conceptual diagram illustrating deposition of a polymeric MLD film using trimethylaluminum (TMA) and aminopropyltrimethoxysilane (APTMOS), according to one embodiment.

FIG. 9 is a diagram illustrating deposition of a polymeric MLD film such as —[Al—(O—Si—O)—($C_3H_6$)—NH]— by exposing 610 the substrate 120 to TMA as a metal-containing precursor and exposing 622 the substrate 120 to 3-APTMOS (3-aminopropyltrimethoxysilane) as an organic precursor (instead of using 4-EPL), according to one embodiment. The substrate 120 is exposed 618, 630 to the reducing agent (e.g., hydrogen radicals H*) after injection of TMA and APTMOS, respectively. As a result, a unit layer 930 is obtained, as illustrated in FIG. 9. The process of exposing the substrate 120 to TMA, H*, APTMOS, and H* may be repeated to stack multiple unit layers 930 on the substrate 120.

Figure 10:
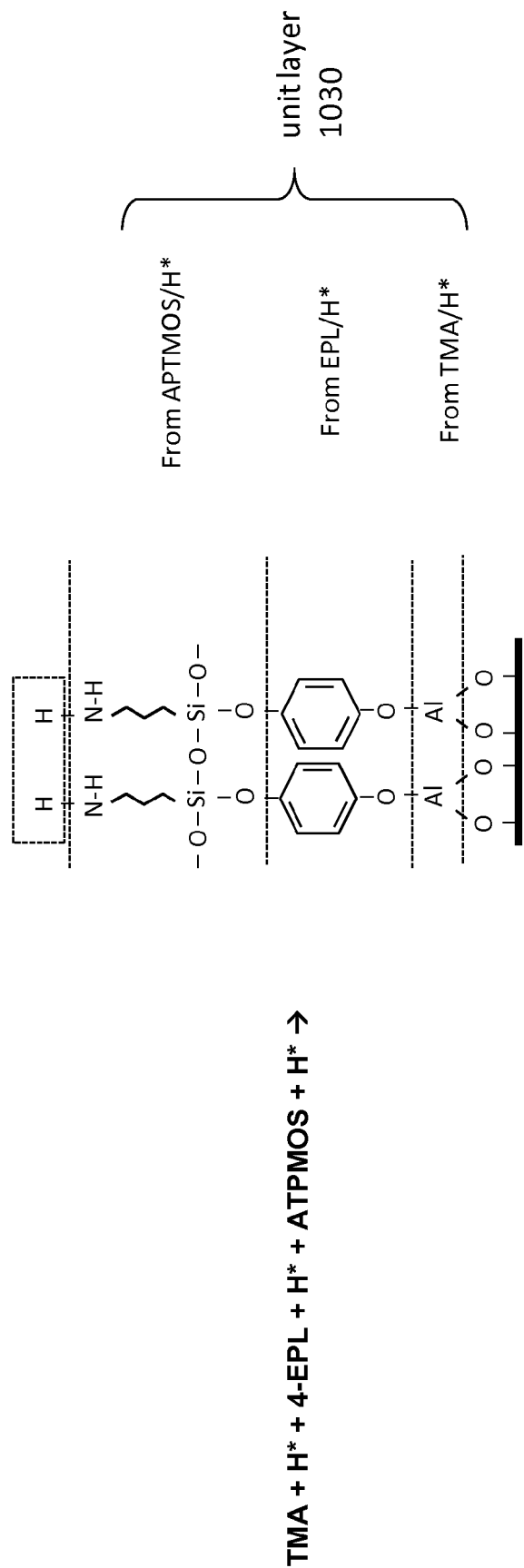
FIG. 10 is a conceptual diagram illustrating deposition of a polymeric MLD film using TMA, 4-ethylphenol and APTMOS, according to one embodiment.

FIG. 10 is a diagram illustrating deposition of a polymeric MLD film with an aromatic benzene ring for longer or larger hydrocarbon bridges such as —[Al—O—($C_6H_4$)—(O—Si—O)—($C_3H_6$)—NH]— by using 4-EPL as a first organic precursor and APTMOS as a second organic precursor. A "longer" hydrocarbon bridge refers to a hydrocarbon bridge comprised of longer unit layers, and a "larger" hydrocarbon bridge refers to a hydrocarbon bridge comprised of unit layers formed by larger molecules and/or ligands. By sequentially exposing the substrate 120 to TMA, hydrogen radicals H*, 4-EPL, hydrogen radicals H*, APTMOS, and hydrogen radicals H*, a unit layer 1030 with an aromatic benzene ring for longer or larger hydrocarbon bridges such as —[Al—O—($C_6H_4$)—(O—Si—O)—($C_3H_6$)—NH]— is formed on the substrate 120. The same process of exposing the substrate 120 to the precursors and radicals may be repeated to stack multiple unit layers 1030 on the substrate 120. In another embodiment, the order of the organic precursors is switched, so the substrate 120 is sequentially exposed to TMA, hydrogen radicals H*, APTMOS, hydrogen radicals H*, 4-EPL, and hydrogen radicals H*.

Figure 11:
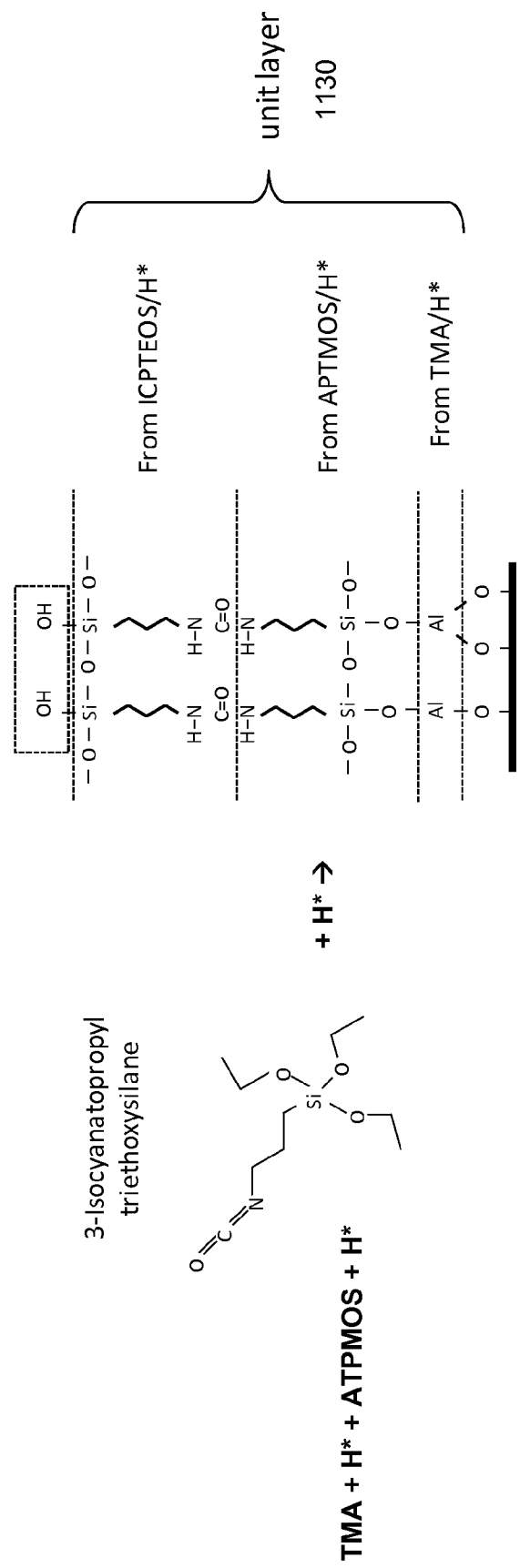
FIG. 11 is a conceptual diagram illustrating deposition of a polyurea-based polymeric film using TMA, APTMOS, and 3-isocyanatopropyltriethoxysilane, according to one embodiment.

FIG. 11 is a diagram illustrating deposition of a polyurea-based MLD film or polyurethane-like MLD film such as —[Al—(O—Si—O)—$C_3H_6$—(NH—(C=O)—NH)—$C_3H_6$—(O—Si—O)—O]— by using APTMOS as a first organic precursor and 3-isocyanatopropyltriethoxysilane (ICPTEOS) as a second organic precursor. By sequentially exposing the substrate to TMA, hydrogen radicals H*, APTMOS, hydrogen radicals H*, ICPTEOS, and hydrogen radicals H*, a unit layer 1130 for longer hydrocarbon bridges such as —[Al—(O—Si—O)—$C_3H_6$—(NH—(C=O)—NH)—$C_3H_6$—(O—Si—O)—O]— is formed on the substrate 120. The process may be repeated to deposit multiple unit layers 1130 on the substrate 120. In another embodiment, the order of the organic precursors is switched, so the substrate 120 is sequentially exposed to TMA, hydrogen radicals H*, ICPTEOS, hydrogen radicals H*, APTMOS, and hydrogen radicals H*.

Further, although the above embodiments are described primarily with respect to depositing Alucone using TMA and 4-EPL, other metalcones such as Zincones and Titanicones can also be deposited using the radicals of reducing agent. Zincone can be deposited, for example, using diethylzinc as a metal-containing precursor, various organic compounds such as ethylene glycol (EG), 4-EPL, or butanediol as an organic precursor, and hydrogen radicals H* as a reducing agent. Titanicone can be deposited, for example, using TEMATi, TDMAT, or titanium tetrachloride as a metal-containing precursor; glycerol, EG, or butanediol as an organic precursor; and hydrogen radicals H* from a reducing agent. precursor Zircone can be deposited, for example, using TEMAZr or TDMAZ as a metal-containing precursor; glycerol, EG, or butanediol as an organic precursor; and hydrogen radicals H* from a reducing agent.

Although the present invention has been described above with respect to several embodiments, various modifications can be made within the scope of the disclosure. Accordingly, the disclosure described above is intended to be illustrative, but not limiting.

What is claimed is:

1. A method for depositing material onto a substrate, the method comprising:
   (a) exposing the substrate to a metal-containing precursor to adsorb metal atoms of the metal-containing precursor to the substrate;
   (b) exposing the substrate injected with the metal-containing precursor to an organic precursor to deposit a layer of material by a reaction of the organic precursor with the metal atoms adsorbed to the substrate; and
   (c) exposing the substrate to radicals of a reducing agent to increase reactivity of the material deposited on the substrate.

2. The method of claim 1, further comprising exposing the substrate to radicals of the reducing agent to increase reactivity of the metal atoms with the organic precursor after injecting the metal-containing precursor onto the substrate and before injecting the organic precursor.

3. The method of claim 1, further comprising repeating (a) through (c) to deposit additional layers of the material onto the substrate.

4. The method of claim 1, wherein the deposited material is metalcone.

5. The method of claim 1, further comprising passing a gas of the reducing agent between electrodes, a voltage difference applied to the electrodes.

6. The method of claim 1, wherein the metal-containing precursor comprises at least one of an aluminum-containing precursor, a titanium-containing precursor, a zinc-containing precursor, a zirconium-containing precursor, a nickel-containing precursor, or a combination thereof.

7. The method of claim 1, wherein the organic precursor comprises at least one of an amino alcohol, an alkyl diamine, an alkyl phenol, an amino alkyl trialkoxy silane, and an isocyanato alkyl trialkoxy silane.

8. The method of claim 1, wherein the reducing agent comprises at least one of hydrazine, ammonia, and hydrogen gas.

9. The method of claim 1, wherein exposing the substrate to radicals of the reducing agent comprises injecting nitrogen gas to stabilize the reducing agent.

10. The method of claim 1, wherein exposing the substrate to the organic precursor comprises:
    exposing the substrate injected with the metal-containing precursor to a first organic precursor to deposit the layer of material by a reaction of the first organic precursor with the metal atoms adsorbed to the substrate;
    exposing the substrate to radicals of the reducing agent to increase reactivity of the material deposited on the substrate with a second organic precursor after exposing the substrate to the first organic precursor; and
    exposing the substrate injected with the first organic precursor to the second organic precursor to retain or lengthen hydrocarbon bridges of the deposited layer of material.

11. An apparatus for depositing a layer of material onto a substrate, the apparatus comprising:
    a first injector having a first reaction chamber opening towards a surface of a substrate to inject a metal-containing precursor onto the substrate and to cause metal atoms of the metal-containing precursor to adsorb to the surface of the substrate;
    a moving mechanism configured to cause a relative movement between the substrate and the first injector;
    a second injector on a path of the relative movement, the second injector having a second reaction chamber opening towards the surface of the substrate to inject an organic precursor onto the surface of the substrate injected with the metal-containing precursor and to deposit a layer of material onto the substrate by a reaction of the organic precursor with the metal atoms adsorbed to the substrate; and
    a radical reactor on the path of the relative movement, the radical reactor configured to generate and inject radicals of a reducing agent onto the substrate injected with the organic precursor.

12. The apparatus of claim 11, wherein the first injector is formed with an exhaust portion and a constriction zone connecting the exhaust portion and the first reaction chamber, a width of the first reaction chamber parallel to the path of the relative movement exceeding a height between an upper surface of the constriction zone and the surface of the substrate.

13. The apparatus of claim 11, further comprising a third injector on the path of the relative movement, the third injector configured to inject an inert gas onto the substrate to remove the metal-containing precursor physisorbed on the substrate.

* * * * *